(12) United States Patent
Romanczyk, Jr. et al.

(10) Patent No.: US 6,743,450 B2
(45) Date of Patent: Jun. 1, 2004

(54) EXTRACTION OF STEROLS FROM COCOA HULLS

(75) Inventors: Leo J. Romanczyk, Jr., Hackettstown, NJ (US); Craig McClelland, E. Stroudsburg, PA (US)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 09/833,134

(22) Filed: Apr. 11, 2001

(65) Prior Publication Data

US 2002/0048613 A1 Apr. 25, 2002

Related U.S. Application Data

(60) Provisional application No. 60/197,134, filed on Apr. 14, 2000.

(51) Int. Cl.$^7$ .............................................. A61K 35/78
(52) U.S. Cl. ........................................ 424/769; 424/776
(58) Field of Search ................................ 424/769, 776

(56) References Cited

U.S. PATENT DOCUMENTS

| | | | | |
|---|---|---|---|---|
| 2,176,031 A | * | 4/1939 | Musher | |
| 4,352,746 A | | 10/1982 | Bracco et al. | 252/398 |
| 4,908,212 A | | 3/1990 | Kwon et al. | 424/440 |
| 4,999,185 A | * | 3/1991 | Takemori et al. | |
| 5,147,672 A | | 9/1992 | McLachlan et al. | 426/241 |
| 5,157,132 A | | 10/1992 | Tan et al. | 549/413 |
| 5,190,618 A | | 3/1993 | Top et al. | 203/34 |
| 5,252,729 A | | 10/1993 | De Crosta et al. | 540/18 |
| 5,371,245 A | | 12/1994 | Rindone et al. | 549/413 |
| 5,424,457 A | | 6/1995 | Sumner, Jr. et al. | 549/408 |
| 5,487,817 A | | 1/1996 | Fizet | 203/38 |
| 5,614,242 A | | 3/1997 | Fox | 426/549 |
| 5,616,735 A | | 4/1997 | Hunt | 549/413 |
| 5,646,311 A | | 7/1997 | Hunt et al. | 549/413 |
| 5,660,691 A | | 8/1997 | Barnicki et al. | 203/72 |
| 5,670,669 A | | 9/1997 | Hunt | 549/413 |
| 5,703,252 A | | 12/1997 | Hunt et al. | 549/413 |
| 5,824,354 A | | 10/1998 | Ritter et al. | 426/417 |
| 5,880,300 A | | 3/1999 | Kodali | 554/190 |
| 5,908,940 A | | 6/1999 | Lane et al. | 549/413 |
| 6,159,451 A | | 12/2000 | Kim et al. | 424/58 |
| 2003/0206981 A1 | | 11/2003 | Lee et al. | 424/776 |

FOREIGN PATENT DOCUMENTS

| | | |
|---|---|---|
| EP | 0 861 600 | 9/1998 |
| GB | 2 223 944 | 4/1990 |
| SU | 1734748 | * 5/1992 |
| WO | WO 99/63031 | 12/1999 |
| WO | WO 01/79400 | 10/2001 |

OTHER PUBLICATIONS

Gavrilenko, I. Maslo–Zhir. Prom–st. 1977. vol. 8, pp. 36–37. CAPLUS Abstract enclosed.*

The Condensed Chemical Dictionary, 10th ed. 1981. Van Nostrand Reinhold Co. p. 792.*

Carpenter, D.R., et al., "Lipid Composition of *Herrania* and *Theobroma* Seeds", *JAOCS*, vol. 71, No. 8, 1994.

El–Saied, H. et al., "Composition of cocoa shell fat as related to cocoa butter", Z. *Ernahrungswissenschaft*, 1981, 145–151.

Warocquier–Clerout et al., "Non–saponifiable fraction of cocoa shell butter: effect on rat and human skin fibroblasts", *International Journal of Cosmetic Science*, 1992, 14, 39–46.

Mueller, "Antioxidantive Properties of Cacao and Their Effect on Butteroil", *J. Diary Sci.*, 37:754–759 (1954).

Naito, Fractionation of Antioxidants from Cocoa Husk:, J. Jap. Soc. Food Sci. Technol. 29:529–533 (1982).

* cited by examiner

*Primary Examiner*—Christopher R. Tate
(74) *Attorney, Agent, or Firm*—Clifford Chance, LLP; Margaret B. Kelley

(57) ABSTRACT

Cocoa oils containing phytosterols and tocols are prepared by extracting the cocoa hulls from dried unfermented or fermented cocoa beans, micronized cocoa beans, or roasted beans with a solvent such as petroleum ether and then removing the solvent. The cocoa oils are useful in foods, dietary supplements, pharmaceuticals, and cosmetics.

17 Claims, No Drawings

EXTRACTION OF STEROLS FROM COCOA HULLS

CROSS REFERENCE TO RELATED APPLICATION

This application claims the benefit of filing date of U.S. provisional application Serial No. 60/197,134 entitled EXTRACTION OF STEROLS FROM COCOA HULLS which was filed on Apr. 14, 2000.

BACKGROUND OF THE INVENTION

1. Field of the Invention

This invention is directed to the extraction of valuable by-products from cocoa hulls.

2. Description of Related Art

Cocoa hulls are a waste by-product of the roasting of cocoa beans and have little value in chocolate manufacturing. Generally, the cocoa hulls are used as compost.

Seventeen Herrania and 22 Theobroma species have been described. See Schultes, R. E., *J. Arnold Arb.*, 39:216, 1958; Cuatrescasas J., *Cont. Nat. Herb.* (USA), 35:379, 1964; and Wood, G. A. R. and R. A. Lass, Cocoa, 4$^{th}$ edn., Longman Inc., New York, 1985, pp. 11–37. Of these, *Theobroma cacao* is the only species of major economic importance because its fat rich seeds are the unique source of cocoa solids and cocoa butter used by the confectionery industry. Cocoa beans are produced by cocoa trees which are found in warm, moist climates in areas about 20 degrees latitude north and south of the Equator. In general, the seeds of the *Theohroma cacao* (of the order Sterculiacae) are known chiefly in two varieties: Criollo and Forastero, with Forastero divided into several varieties. A third group, called Trinitario, is essentially a cross between Criollo and Forastero and is not found in the wild. Criollo beans are pale brown in color while Forastero beans are a purple hue. The cocoa tree produces leaves, flowers and fruit throughout the year, and the ripe fruit or pod resembles a long cantaloupe, typically containing from about 20 to 40 almond-shaped cocoa beans.

The cocoa bean is comprised of an inner nib portion covered by an outer shell, also referred to as the hull. On a dry basis, the shell of the bean comprises about 12 to 15% of the weight of the bean, while the nib and residual moisture amounts to approximately 85 to 88%. Typical analytical data ranges for chemical components of cocoa nib are: fat content of 48 to 57%; theobromine content of 0.8 to 1.3%; caffeine content of 0.1 to 0.7%; total nitrogen content of 2.2 to 2.5%; ash content of 2.6 to 4.2%; and water content of 2.3 to 3.2% (see *Pearson's Composition and Analysis of Foods, 9$^{th}$ Edition*, 1991).

Various processes are traditionally employed to extract cocoa butter and cocoa solids from commercial cocoa beans. Typical methods of processing cocoa beans include the steps of (a) bean cleaning; (b) bean roasting; (c) bean winnowing; (d) nib grinding; (e) liquor pressing to produce cocoa butter and cocoa cake, also referred to as partially defatted cocoa solids; (f) optionally cake alkalizing; and (d) cake milling.

The initial step of typical cocoa bean processing methods consists of cleaning the beans to remove extraneous non-cocoa materials. Conventional bean cleaning separates beans from extraneous non-cocoa materials by either size or density using a cleaning machine which is a gravity, vibratory or aspiration table (See *Chocolate, Cocoa and Confectionery: Science and Technology, 3$^{rd}$ Ed.*, by Bernard W. Minifie, page 35; *Chocolate Production and Use, 3$^{rd}$ Ed.*, by L. Russell Cook, page 144–146; and *Industrial Chocolate Manufacture and Use, 2$^{nd}$ Ed.*, by S. T. Beckett, page 55.

In most conventional processes, roasting of the whole bean or nib is an essential step in the manufacture of chocolate or cocoa. Roasting develops the natural flavor and aroma of the cocoa beans, and also loosens the shell so that it can be readily removed during the winnowing process. The degree of cocoa roast is a time/temperature dependent relationship, where the time can vary from 5 to 120 minutes and the temperature of the whole bean can typically vary from 125° C., and with respect to the roasting of nibs, an initial drying process step can be at just below 100° C. to remove the shell, with second stage roasting of nibs alone being at elevated temperatures up to about 130° C.; all of which depend on the construction of the machine, size of the batch and final product desired (see *Chocolate, Cocoa and Confectionery: Science and Technology, 3$^{rd}$ Ed.*, by Bernard W. Minifie, especially page 37, 45–46; *Chocolate Production and Use. 3$^{rd}$ Ed.*, by L. Russell Cook, page 146–152; and *Industrial Chocolate Manufacture and Use, 2$^{rd}$ Ed.*, by S. T. Beckett, page 55–64) hereby incorporated by reference). U.S. Pat. No. 5,252,349 to Carter, Jr., hereby incorporated by reference), involves heating the bean to a temperature of about 152° C. to 160° C. for about 5 to 8 minutes.

An alternative method for directly processing cocoa beans to cocoa butter and partially defatted cocoa solids is disclosed in U.S. Pat. No. 6,015,913 (issued Jan. 18, 2000 to Kealey et al.), the disclosure of which is incorporated herein by reference. The method involves heating the cocoa beans for a time and at an internal bean temperature sufficient to loosen the cocoa shell without roasting the nib, winnowing the nibs from said shells, and screw pressing the nibs to produce cocoa butter and partially defatted cocoa solids. Typically, the internal bean temperature is about 100–110° C., preferably less than about 105° C. and typically, the heating is carried out by infra red heating in a micronizer. The winnowing is carried out in an air fluidized bed density separator. The loss of cocoa polyphenols including cocoa procyanidins is minimized because the temperatures used are lower than those used in a process.

The winnowing operation serves to separate the beans into the desired inner portion of the bean (nib) and the outer portion of the bean (shell or hull). The principle of separation by a winnowing process depends on the difference in the apparent density of the nib and of the shell. Standard winnowing machines make use of the combined action of sieving and air aspiration. As discussed earlier, the shell is loosened during the conventional roasting step and/or other heating or drying steps. After loosening, the beans are typically broken between rollers or such devices to shatter the cocoa beans along natural fracture lines of the cocoa nib to facilitate shell removal during winnowing (see U.S. Pat. No. 2,417,078 to Jones. U.S. Pat. No. 5,252,349 to Carter, Jr., hereby incorporated by reference. *Chocolate, Cocoa and Confectionery: Science and Technology, 3$^{rd}$ Ed.*, by Bernard W. Minifie. pp. 47–51; *Chocolate Production and Use, 3$^{rd}$ Ed.*, by L. Russell Cook. pp. 152–153; and *Industrial Chocolate Manufacture and Use, 2$^{nd}$ Ed.*, by S. T. Beckett, page 67–68.

Some cocoa bean processing techniques include the use of thermal pre-treatment equipment to aid in the separation of the shell from the nib. This involves giving the beans a thermal shock by hot air, steam or infra-red heat (see U.S. Pat. No. 4,322,444 to Zuilichem et al., and British Patent No. 1,379,116 to Newton, *Chocolate, Cocoa and Confectionery: Science and Technology, 3$^{rd}$ Ed.*, by Bernard W. Minifie page 44–45; *Chocolate Production and Use. 3rd Ed.*, by L. Russell Cook, page 155; and *Industrial chocolate Manufacture and Use, 2nd Ed,.* by S. T. Beckett, page 60–62, hereby incorporated by reference).

Infra-red pre-treatment uses infra-red heating to rapidly heat and expand the beans which assists in loosening the shells. The method consists of treating the beans with infra-red radiation for a period between one-half and two minutes, during which time the beans are typically heated to a temperature of about 100 to 110° C. The infra-red radiation used has a wavelength between 2 and 6 microns which corresponds to a frequency in the range of 0.7 to $1.2 \times 10^8$ megacycles per second. This energy penetrates and excites the molecules of the bean which causes them to vibrate at their own frequency and results in rapid heating of the beans.

Cocoa hulls resulting from the above processes are removed from further cocoa/chocolate manufacturing steps. As such, the cocoa hulls are considered a waste by-product with little economic value, although they are used for mulching or composting applications.

SUMMARY OF THE INVENTION

As used herein, the term "phytosterols" refers to lipid mixtures obtained from a plant source containing free or bound sterols. A cocoa oil which contains phytosterols is prepared by extracting cocoa hulls with a solvent for the phytosterols. The phytosterols are a mixture of free and bound sterols, with the free sterols being up to about 90% of the phytosterols present. The phytosterols include campesterol, β-sitosterol, stigmasterol, cycloartanol, 24-methylene cycloartenol, as well as minor amounts of other phytosterols. The bound phytoserols include the fatty acid ester or ferulate derivatives of the phytosterols. The cocoa oil can further comprise tocopherols and tocotrienols which are members of the tocol family.

The process for extracting the cocoa oil comprises the steps of: a) grinding the cocoa hulls; b) extracting the ground cocoa hulls with a solvent for the phytosterols; c) removing the solvent; and d) recovering the cocoa hull oil.

The phytosterol-containing cocoa oil can be included in foods, dietary supplements, pharmaceuticals, and cosmetics.

DETAILED DESCRIPTION OF THE INVENTION

Cocoa beans can be divided into four categories based on their color: predominately brown (fully fermented), purple/brown, purple, and slaty (unfermented). Preferably, as indicated above, the cocoa oil is prepared from underfermented cocoa beans which have a higher cocoa phytosterol content than fermented beans. Underfermented beans include slaty cocoa beans, purple cocoa beans, mixtures of slaty and purple cocoa beans, mixtures of purple and brown cocoa beans, or mixture of slaty, purple, and brown cocoa beans. More preferably, the cocoa beans are slaty and/or purple beans. Underfermented beans typically have a fermentation factor of 275 or less.

The "fermentation factor" is determined using a grading system for characterizing the fermentation of the cocoa beans. Slaty is designated 1, purple is 2, purple/brown is 3, and brown is 4. The percentage of beans falling within each category is multiplied by the weighted number. Thus, the "fermentation factor" for a sample of 100% brown beans would be 100×4 or 400, whereas for a 100% sample of purple beans it would be 100×2 or 200. A sample of 50% slaty beans and 50% purple beans would have a fermentation factor of 150 (50×1)+(50×2).

The preferred solvents are petroleum ether, hexane, pentane, and ethyl ether. The solvent is recovered by vacuum distillation or other conventional methods.

The phytosterols may be purified by preparative high pressure liquid chromatography or column chromatography.

The cocoa oil, particularly the purified cocoa oil, may be useful in foods, as a food additive, in a dietary supplement, or in a pharmaceutical. The cocoa oil may be used with a carrier, a diluent, or an excepient. The carrier, diluent, or excepient selected will depend on the particular end use, for example, for human or veterinary use, whether as a food, food additive, or dietary supplement or in a pharmaceutical.

As used herein a "food" is a material consisting essentially of protein, carbohydrate and/or fat, which is used in the body of an organism to sustain growth, repair and vital processes and to furnish energy. Foods may also contain supplementary substances such as minerals, vitamins and condiments. See Merriam-Webster's Collegiate Dictionary, 10th Edition, 1993. The term food includes a beverage adapted for human or animal consumption. As used herein a "food additive" is as defined by the FDA in 21 C.F.R. 170.3(e)(1) and includes direct and indirect additives. As used herein, a "pharmaceutical" is a medicinal drug. See Merriam-Webster's Collegiate Dictionary, 10th Edition, 1993. A pharmaceutical may also be referred to as a medicament. As used herein, a "dietary supplement" is a product (other than tobacco) that is intended to supplement the diet that bears or contains one or more of the following dietary ingredients: a vitamin, a mineral, an herb or other botanical, an amino acid, a dietary substance for use by man to supplement the diet by increasing the total daily intake, or a concentrate, metabolite, constituent, extract or combination of these ingredients.

The cocoa oil, particularly the purified cocoa oil, may be used in cosmetics. The cosmetics are formulated using conventional methods known in the art. Typical cosmetics include creams, lotions, gels, conditioners, shampoos, soaps. dyes, and other compositions for external use. The cocoa oils may be used with other conventional cosmetically acceptable ingredients such as moisturizers (e.g., cetyl alcohol, dimethicone silicon, isopropyl lanolate, myrisate, or palmitate, lanolin and lanolin alcohols and oils, octyl dodecanol, oleic acid, panthenol, stearic acid, and stearyl alcohol), preservatives (e.g., trisodium and tetrasodium edetate and tocopherol), antioxidants such as vitamins, antimicrobials (e.g., butyl, propyl, ethyl, and methyl parabens, DMDM hydantoin, methylisothiazolinone, phenoxyethanol, and quaternium-15), thickeners (e.g., candelilla, carnuba, and microcrystalline waxes and carbomer and polyethylene thickeness), solvents (e.g., butylene glycol and propylene glycol, cyclomethicone, ethanol, glycerin), emulsifiers (e.g., glyceryl monostearate and lauramide DEA, and polysorbates). color additives such as synthetic organic colors derived from coal and petroleum sources (e.g., D&C Red No. 7 Calcium Lakes) and inorganic pigments (e.g iron oxides and mica), hair dyes such as phenol derivatives (e.g., aminophenols), pH adjusters (e.g., ammonium hydroxide, citric acid, and triethanolamine), and other FDA approved ingredients such as magnesium aluminum silicate, silica, and talc (absorbents), sodium lauryl sulfate (a detergent), stearic acid (a cleansing emulsifier), and zinc stearate (a lubricant).

Sterols, particularly phytosterols, can be used in a variety of products including pharmaceuticals, cosmetics, vitamins, foods, and dietary supplements. The ferulated polysterols are particularly useful as antioxidants.

The sterol amounts reported in the following examples were determined using the analytical procedure described in Rogers et al., "Identification and Quantitation of gamma-Oryzanol Components and Simultaneous Assessment of Tocols in Rice Bran Oil", *J. Amer. Oil Chem. Soc.* 70(30) 1993 and Carpenter, et al., "Lipid Composition of *Herrania and Theobroma Seeds, J. Amer. Oil Chem. Soc.* 71(8) 1994.

EXAMPLES

Example 1

Plant material Pods were obtained from the Centro Agronomico Tropical de Investigacion y Ensenanza (CATIE) germplasm collection at Turrialba, Costa Rica, and from the Comissao Executiva do Plano da Lavoura Cacaueira (CEPLAC) cocoa germplasm collection (Belem, Brazil).

Reagents. Pyridine N,O-bis(trimethylsilyl) trifluoroacetamide (BSTFA)+trimethylchlorosilane, cholesterol, campesterol, stigmasterol, β-sitosterol, α-tocopherol and δ-tocopherot were obtained from Sigma Chemical Company (St. Louis, Mo.). β-tocopherol was obtained from Matreya (Pleasant Gap, Pa.) and gamma-tocopherol from Fluka (Ronkonkoma, N.Y.). Cycloartenol and 24-methylene cycloartanol were purified from hydrolyzed γ-oryzanol (Farmingdale, N.Y.) as described by Rogers et al. (9). Tocotrienols (alpha, beta, and gamma) were a generous gift from Hoffman La Roche (Basel, Switzerland).

Cocoa seeds with pulp removed from Theabroma cocoa pods were freeze-dried on a Labconco (Kansas City, Mo.) Freeze Dry System. The pulp and hulls were manually removed, and the freeze-dried hulls were ground to a fine powder with a Tekmar Mill (Cincinnati, Ohio). The ground mass was subjected to overnight extraction with redistilled petroleum ether (b. p. 38–39.6° C.) in a Soxtec apparatus (Fisher Scientific, Springfield. N.J.). The solvent was carefully removed by slow evaporation under a stream of nitrogen, and the resultant extracts were stored at −40° C.

Gas chromatography of fatty acid methyl esters (FAME). FAME of the extracts described above were prepared by alkali-catalyzed transmethylation. FAME separations were achieved on a 30 m×0.25 mm i.d. Supelco (Bellefonte. Pa.) SP2340 fused-silica capillary column programmed at 90° C. for 3 min., then 5° C./min to 210° C. for 20 min on a Hewlett-Packard (Palo Alto. Calif.) Model 5880A gas chromatograph. The injector and flame ionization detector temperatures were set at 220 and 250° C. respectively. Helium was used as the carrier gas at a linear velocity ($\bar{u}$) of 90 cm/s. One μL injections were split 50:1.

Sterols derivatization. Preweighed samples (0.1 g) of the extracts described above containing cholesterol (0.2 mg) as the internal standard (ISTD) were saponified at 80° C. for 1 h with 0.5 mL of 50% KOH in ethanol. After cooling to room temperature 1.5 mL distilled water was added, and the free sterols were extracted two times with 5 mL redistilled n-hexane. The combined extracts were dried over $Na_2SO_4$ and taken to dryness under a stream of nitrogen. Dry pyridine (0.1 mL) was added, followed by an equal volume of BSTFA reagent. Trimethylsilyl (TMS) ether derivatives of cholesterol, campesterol, stigmasterol, β-sitosterol, cycloartenol and 24-methylene cycloartanol were similarly prepared.

Gas chromatography of sterol-TMS ether derivatives. Sterol-TMS ether derivatives were separated on a 25 m×0.25 mm i.d. Quadrex (New Haven, Conn.) 50% methylphenyl-silicone fused-silica capillary column, programmed at 250° C. for 37 min., then 10° C./min to 300° C. for 5 min on a Hewlett-Packard Model 5890A gas chromatograph. The injector and flame-ionization detector temperatures were set at 250 and 300° C, respectively. Helium was used as the carrier gas at a linear velocity ($\mu$) of 25 cm/s. One μL injections were split 50:1. Quantitation was achieved by the ISTD technique (11). Peak identifications were made by comparison to the retention time ($t_R$) of authentic sterol-TMS ether derivatives and by mass spectral analysis.

Mass spectrometry (Ms). Analyses were performed on a Hewlett-Packard Model 5987A GC-MS System. Electron ionization-MS (El-MS) of the sterol-TMS ether derivatives was performed at 70 eV with a source temperature of 200° C. a scan range of 50–600 amu at a rate of 1.2 scans/s. Chromatographic conditions were identical to those described above.

High performance liquid chromatography (HPLC) of tocols. Analyses were performed on a Hewlett-Packard Model 1090 HPLC System with a Hewlett-Packard Model 1046A programmable fluorescence detector. Tocol separations were achieved on a 25 cm×4.6 mm, 5 Supelcosil (Supelco) LC-Si column held at 45° C. The mobile phase consisted of 8% (by vol) redistilled tert-butyl-methyl ether in redistilled n-hexane at a flow rate of 1.8 mL/min. Components were detected by fluorescence where excitation ($\lambda_{ex}$) and emission ($\lambda_{em}$) wavelengths were set at 290 and 325 nm, respectively. Fifty μL of 2.5% (wt/vol) fat solutions in redistilled n-hexane were injected. Tocols were quantitated by the external standard technique (12), and peak identifications were made by comparison to $t_R$s of authentic tocopherol and tocotrienol standards.

Example 2

A variety of raw materials were analyzed to determine their phytosterol levels using the analytical procedures described in Example 1. The results are shown in Table 1. Most commercial oils, except for rice oil, corn oil, and canola oil, as well as the oils from various nuts were found to contain very low sterol levels. Roasted cocoa hull oils, however, were found to contain nearly three times the sterol levels found in rice bran oils. Rice germ and rice hulls were found to contain nearly double the amount of sterols found in the bran oils, whereas peanut hulls and peanut germ showed increases in sterols, but the levels were still three-fold less than that found in rice bran oils.

Example 3

The effects of fermentation and roasting on the sterol content of the cocoa hulls was determined. The results are shown in Table 2. The results show that roasting did not cause the loss of sterols although there were considerable variations in the amount of oil recovered. The total sterols recovered from three different samples of roasted cocoa hulls fluctuated as a consequence of the amounts of oils recovered from these samples. This data differed from that obtained with unroasted cocoa hulls where two-fold higher sterol levels were found in much lower amounts of extracted oils. It is possible that variable amounts of cocoa fat permeate into the hull which cause variable recoveries and sterol levels.

Example 4

This gross difference does not effectively detail the types of "bound" sterols present in any oil from their "free" forms since "bound" sterols can occur as glycosides, fatty acid esters and ferulates. Any additional analytical information on their distribution and composition will have to be provided by fractionating the oil by chromatography (LSC).

Combined capillary gas chromatography (GC) and gas chromatography 1 mass spectra (GC/MS) analysis were used to examine the sterol composition of the extracted cocoa oils. As shown in FIG. 1, a typical sterol separation was encountered as well as the presence of several unknowns.

Example 5

Capillary Supercritical Fluid Chromatography (CSFC) was also used to determine whether a more effective method could be developed to discriminate between "free" and "bound" sterols (i.e., sterols which are glycosides, fatty acid esters, and/or ferulates). Through the use of authentic standards and standard addition techniques, clusters of peaks were identified as the free fatty acid, and mono-, di- and triglyceride portions of the oil. See FIG. 2 for details of the separation which was carried out on a Lee Scientific Supercritical Fluid Chromatograph.

After saponification, another more pronounced cluster of peaks occurred. This particular cluster represented the total sterols (free and hydrolyzed) present in each oil. These results show that the CSFC separation is useful to assay unsaponified oils for "free" sterols content and after saponification, to assay for the total sterols content. The difference between the two values is the amount of "bound" sterols present in the oil. However, the CSFC separation did not possess the resolution capability to separate each individual sterol as well as by HRGC. As a consequence, it is possible that components other than the sterols can be present in this cluster. The method of Example 3 was therefore used to quantitate total sterols in saponified oils and the CSFC was used to quantitate "free" sterols in unsaponified oils.

A comparison of the two sets of data appears in Table 3. It was found that rice bran oil contained the highest level of "bound" sterols, while olive oil contained essentially all "free" sterols. Considerable variation existed among the other oils. The roasted cocoa hull oil contained approximately 10% "bound" sterols.

Example 6

The cocoa hull oil can be subjected to liquid-solid chromatography (LSC) to obtain various fractions containing components of different polarity. A typical LSC fractionation consists of eluting 100 mg of the oil through a short column of silica gel (40 μ particle size) pre-equilibrated with hexane. An elutropic elution starts with hexane followed by incremental amounts of diethyl ether in hexane. Three column void volumes are collected for each change of solvent and ten fractions are collected. Each fraction is concentrated under nitrogen and chromatographed by CSFC. The same fractions are then saponified and rechromatographed by CSFC to determine which fraction produces hydrolyzable sterols. Through this process, a particular LSC fraction was found to be enriched with "bound" sterols. The CSFC chromatography of this fraction indicated a cluster of components which coeluted with part of the triglyceride fraction.

This fraction was then reconcentrated and subjected to mass spectrometry via a direct insertion probe. The resultant mass spectrum should produce a distinguishing cluster of even molecular ions. An expanded view of part of this spectrum is shown in FIG. 3 along with a printout of the individual ion intensities. It is recognized that some of these even ions may be the molecular ions for different "bound" sterols. Hence, a determination of even mass fragmentation ions corresponding to calculated molecular weights of sterols esterified to ferulic acid and various fatty acids are presented in Table 5. On the basis of the ion intensity data, estimate of the relative abundance for each "bound" sterol can be determined. It should be noted that several "bound" sterols are possible based on the molecular weight calculation (see the sterols having molecular weights of 664, 676, 678).

Now that the preferred embodiments of the invention have been described in detail, various modifications and improvements thereon will become readily apparent to the practitioner. Accordingly, the spirit and scope of the present invention are to be limited only by the appended claims, and not by the foregoing specification.

TABLE 1

| | | | | mg Sterols/100 g Oil | | | | | |
|---|---|---|---|---|---|---|---|---|---|
| Sample | Campesterol | Stigmasterol | 24-Methyl Cholestanol 3-β-ol | β-Sitosterol | Obtusifoliol | Stigmastenol | Cycloartenol | 24-Methylene Cycloartanol | Total Sterols |
| Rice Bran Oils | | | | | | | | | |
| Batch A | 241 | 188 | 41 | 763 | UR | 91 | 227 | 35 | 1,586 |
| Batch B | 300 | 221 | 45 | 909 | UR | 92 | 256 | 104 | 1,927 |
| Batch C | 248 | 174 | 38 | 704 | UR | 69 | 290 | 140 | 1,663 |
| Rice Germ* | 540 | 225 | 26 | 1027 | 119 | 96 | 699 | 534 | 3,263 |
| Rice Hull* | 394 | 398 | ND | 943 | ND | 691 | 556 | 313 | 3,295 |
| Olive Oil | Trace | Trace | ND | 78 | Trace | 25 | Trace | ND | 103 |
| Soybean Oil | 67 | 58 | ND | 158 | Trace | Trace | Trace | ND | 281 |
| Canola Oil | 205 | Trace | ND | 351 | ND | Trace | ND | ND | 556 |
| Corn Oil | 294 | 170 | Trace | 607 | ND | 24 | 163 | 200 | 1,458 |
| Peanut Oil | 28 | Trace | Trace | 117 | Trace | Trace | Trace | Trace | 145 |
| Peanut Hull* | 88 | 44 | ND | 433 | ND | ND | ND | ND | 565 |
| Peanut Germ* | 144 | 29 | ND | 479 | Trace | 38 | ND | ND | 690 |
| Almond* | ND | ND | ND | 223 | ND | ND | ND | ND | 223 |
| Hazelnut* | ND | ND | ND | 114 | ND | ND | ND | ND | 114 |
| Oat Bran* | 26 | Trace | ND | 184 | Trace | Trace | Trace | 20 | 230 |
| Cocoa Butter | Trace | 69 | ND | 136 | UR | Trace | ND | ND | 205 |
| Cocoa Hulls* | 572 | 478 | ND | 3,288 | ND | 37 | 263 | 36 | 4,674 |

TABLE 1-continued mg Sterols/100 g Oil

| Sample | Campesterol | Stigmasterol | 24-Methyl Cholestanol 3-β-ol | β-Sitosterol | Obtusifoliol | Stigmastenol | Cycloartenol | 24-Methylene Cycloartanol | Total Sterols |
|---|---|---|---|---|---|---|---|---|---|

*Oils obtained by Soxhlet extraction with petroleum ether
UR — Unresolved component
ND — Not detected
Trace — less than 20 mg sterol/100 g of oil

TABLE 2 mg Sterol/100 g Oil

| Sample | % Oil Recovered | Campesterol | Stigmasterol | beta-Sitosterol | Stigmastenol | Cycloartenol | 24-Methylene Cycloartenol | Total Sterols |
|---|---|---|---|---|---|---|---|---|
| Roasted Cocoa Hulls | | | | | | | | |
| Batch A | 3.05 | 572 | 478 | 3,288 | 37 | 263 | 36 | 4,674 |
| Batch B | 10.05 | 88 | 176 | 561 | Trace | 26 | Trace | 851 |
| Batch C | 2.60 | 562 | 578 | 3,049 | Trace | 186 | Trace | 851 |
| Hulls from sun-dried Brazilian cocoa beans fermented for 1 day | 0.65 | 997 | 1,461 | 5,832 | 27 | 145 | Trace | 8,462 |
| Hulls from sun-dried Brazilian cocoa beans fermented for 3 days | 1.03 | 1,245 | 1,451 | 7,092 | 308 | 368 | 21 | 10,485 |
| Hulls from sun-dried Brazilian cocoa beans fermented for 5 days | 0.61 | 109 | 511 | 3,180 | Trace | 161 | Trace | 3,961 |

Trace = less than 20 mg sterol/100 g oil

TABLE 3

Sterol Levels in Saponified and Unsaponified Cocoa Oils

| | mg Sterols/100 gm Oil | | Percent "Free" Sterols |
|---|---|---|---|
| Sample | Unsaponified[1] | Saponified[2] | Present in Oil |
| Rice Bran Oil | 209 | 1,663 | 13 |
| Rice Germ Oil | 658 | 3,263 | 20 |
| Olive Oil | 117 | 113 | ~100 |
| Canola Oil | 172 | 556 | 31 |
| Corn Oil | 277 | 1,458 | 20 |
| Soybean Oil | 197 | 283 | 70 |
| Oat Bran Oil | 82 | 230 | 36 |
| Cocoa Butter | 86 | 205 | 42 |
| Roasted Cocoa Hull Oil | 4,396 | 4,674 | 94 |

[1]CSFC Analysis
[2]Method of Example 1

TABLE 4

Possible "Bound" Sterol Structures Which Can Be Determined by Mass Spectrometry

| Calculated Molecular Weight | Corresponding Possible "Bound" Sterol Structure |
|---|---|
| 576 | Campesteroyl ferulate |
| 590 | β-Sitosteroyl ferulate |
| 602 | Cycloartenoyl ferulate |
| 650 | Stigmasteroyl palmitate |
| 662 | Campesteroyl linoleate |
| 664 | Cycloartenoyl palmitate or Campesteroyl oleate |
| 674 | Stigmasteroyl linoleate |
| 676 | Stigmasteroyl oleate or β-Sitosteroyl linoleate |
| 678 | 24-Methylene cycloartanoyl palmitate or β-Sitosteroyl oleate or Stigmasteroyl stearate |
| 688 | Cycloartenoyl linoleate |
| 690 | Cycloartenoyl oleate |
| 702 | 24-Methylene cycloartanoyl linoleate |

What is claimed:

1. A cocoa oil, extracted from cocoa hulls, which oil comprises free and bound phytosterols and tocols, wherein the free phytosterols comprise campesterol, β-sitosterol, stigmasterol, and cycloartenol, and wherein the tocols comprise tocopherols and tocotrienols, which oil is prepared by:
    (a) grinding cocoa hulls from dried cocoa beans;
    (b) extracting the ground cocoa hulls with a solvent that dissolves the phytosterols and the tocols;
    (c) removing the solvent; and
    (d) recovering the cocoa oil.
2. The oil of claim 1, wherein the free sterols are up to about 90% of the phytosterols present in the oil.

3. The oil of claim 2, wherein the bound phytosterols are the fatty acid esters or ferulate derivatives of the phytosterols.

4. The oil of claim 1, wherein the cocoa hulls are from non-roasted cocoa beans.

5. The oil of claim 1, wherein the cocoa hulls are from roasted cocoa beans.

6. The oil of claim 1, wherein the cocoa hulls are from Theabroma cacao.

7. The oil of claim 1, wherein the cocoa beans are unfermented or fermented cocoa beans.

8. The oil of claim 1, wherein the cocoa beans are freeze dried.

9. A process for extracting a cocoa oil comprising free and bound phytosterols and tocols, wherein the free phytosterols comprise campesterol, β-sitosterol, stigmasterol, and cycloartenol and wherein the tocols comprise tocopherols and tocotrienols, which process comprises the steps of:

(a) grinding cocoa hulls from dried cocoa beans;

(b) extracting the ground cocoa hulls with a solvent that dissolves the phytosterols and the tocols;

(c) removing the solvent; and (d) recovering the cocoa oil.

10. The process of claim 9, wherein the solvent is selected from the group consisting of petroleum ether, hexane, pentane, and ethyl ether.

11. The process of claim 9, wherein the solvent is petroleum ether.

12. The process of claim 9, wherein the solvent is recovered by vacuum distillation.

13. The process of claim 9, wherein the cocoa hulls are from unfermented or fermented cocoa beans.

14. The process of claim 9, wherein the cocoa hulls are from micronized cocoa beans dried by micronizing.

15. The process of claim 9, wherein the cocoa hulls are from roasted cocoa beans.

16. The process of claim 9, wherein the cocoa hulls are from Theobroma cacao.

17. The process of claim 9, wherein the cocoa beans are freeze dried.

* * * * *